(12) United States Patent
Wellhöfer et al.

(10) Patent No.: US 8,337,018 B2
(45) Date of Patent: Dec. 25, 2012

(54) SURGICAL MICROSCOPE

(75) Inventors: Armin Wellhöfer, Schwaig (DE); Christof Donitzky, Eckental/Eschenau (DE)

(73) Assignee: Wavelight GmbH, Erlangen (DE)

( * ) Notice: Subject to any disclaimer, the term of this patent is extended or adjusted under 35 U.S.C. 154(b) by 11 days.

(21) Appl. No.: 12/965,334

(22) Filed: Dec. 10, 2010

(65) Prior Publication Data

US 2012/0147325 A1 Jun. 14, 2012

(51) Int. Cl.
*A61B 3/14* (2006.01)
*A61B 3/10* (2006.01)

(52) U.S. Cl. ............ 351/206; 351/216; 351/212

(58) Field of Classification Search .......... 351/20–246
See application file for complete search history.

(56) References Cited

U.S. PATENT DOCUMENTS

| | | | | |
|---|---|---|---|---|
| 4,964,715 A | * | 10/1990 | Richards | 351/212 |
| 5,080,477 A | * | 1/1992 | Adachi | 351/212 |
| 7,883,505 B2 | * | 2/2011 | Van Heugten et al. | 606/4 |
| 2005/0020876 A1 | * | 1/2005 | Shioda et al. | 600/101 |

* cited by examiner

*Primary Examiner* — Mohammed Hasan
(74) *Attorney, Agent, or Firm* — Keiko Ichiye

(57) ABSTRACT

A surgical microscope (10) comprises an image display module for displaying an image to be overlaid into an observation beam path of the microscope, and an image sensor for recording an image of an eye (30) of an observer looking through the microscope. According to the invention, the image display module and the image sensor are formed by a common electronic module (28) produced in integrated circuit technology. The module (28) preferably has an organic light-emitting diode, produced in OLED-on-CMOS technology, for displaying the image to be overlaid. The image sensor may be formed by CMOS-compatible photodetectors.

17 Claims, 2 Drawing Sheets

SURGICAL MICROSCOPE

TECHNICAL FIELD

The present invention relates to ophthalmic surgical microscopes, and, more particularly, to a surgical microscope comprising an image display module for displaying an image to be overlaid into an observation beam path of the microscope and an image sensor for recording an image of an eye of an observer looking through the microscope.

BACKGROUND

Surgical microscopes are used, for example, as an aid in operations on the human eye, for instance in laser treatment of the eye in order to ablate corneal tissue or to make cuts in the cornea or other parts of the eye. So that the operator has his hands free during the operation and to keep the operator's hand from being contaminated by touching actuation elements of the microscope or other controllable components used during the operation, it is known in the prior art to overlay an image into the observation beam path of the surgical microscope, which represents a control menu on which the operator (observer) can visually (i.e. by controlled viewing) select and activate individual control functions. To this end it is necessary to detect the observer's viewing direction, for which purpose in the prior art a camera is provided, for example having a CCD sensor. A beam is in this case extracted from the observation beam path of the microscope and directed onto the camera. Using suitable image analysis algorithms, the details of which are not of further interest in the scope of the invention, it is possible to determine the observer's viewing direction relative to the overlaid control menu. Depending on where the observer is looking at on the overlaid control menu, it is possible for the observer to activate different functions.

By way of example, in respect of the prior art relating to surgical microscopes which are equipped with devices for overlaying a control menu and for detecting the direction in which an observer looks at the overlaid control menu, reference may be made to WO 96/13743 A1. There, the control menu is displayed on an LCD screen and overlaid into the observation beam path by means of suitable optical elements. In order to record the pupil position of the observer's eye, a CCD camera is provided.

SUMMARY

By contrast, a surgical microscope of the generic type referred to in the introduction is distinguished according to the present invention in that the image display module and the image sensor are formed by a common electronic module produced in integrated circuit technology. Integrating the image display module and the image sensor into a common electronic module (semiconductor chip) achieves an extremely compact design of the surgical microscope. In particular, it is not necessary to provide separate beam paths for overlaying the image generated by the image display module and for extracting the image of the observer's eye to be sent onto the image sensor. The two images can instead be guided in a common beam path, which correspondingly requires only a single beam guiding section (for example a tube) of a housing of the surgical microscope.

A second observation tube of the surgical microscope can thus remain free for a co-observer, for example an assistant. In this way, the operation can be carried out without interruption.

In one embodiment, the module integrating the image display module and the image sensor is produced in the CMOS technology and has image display elements which are formed by organic light-emitting diodes (abbreviated to OLEDs). An OLED-on-CMOS technology has recently been developed and has proven suitable for the production of OLED display units in integrated circuit technology. By using CMOS-compatible photodetectors, such an OLED-on-CMOS chip can then be expanded to form a combined display/camera chip, in which case the photodetectors and the OLED image display elements may for example be arranged in the manner of two interleaved matrices. Nevertheless, a configuration of this display/camera chip in which various regions of the chip surface are provided exclusively for the OLED image display elements and other regions are provided exclusively for the photodetectors, so as to create mutually separated areas for the image display and the image acquisition are also contemplated by the present invention.

The embodiments of the surgical microscope of the present invention can further comprise an electronic control arrangement, the control arrangement being adapted to analyse the image recorded by the image sensor with regard to the observer's viewing direction and to control one or more controllable components as a function of the detected viewing direction of the observer.

BRIEF DESCRIPTION OF THE DRAWINGS

The invention will be explained in more detail below with the aid of the appended drawings, in which.

DETAILED DESCRIPTION

Figure 1:
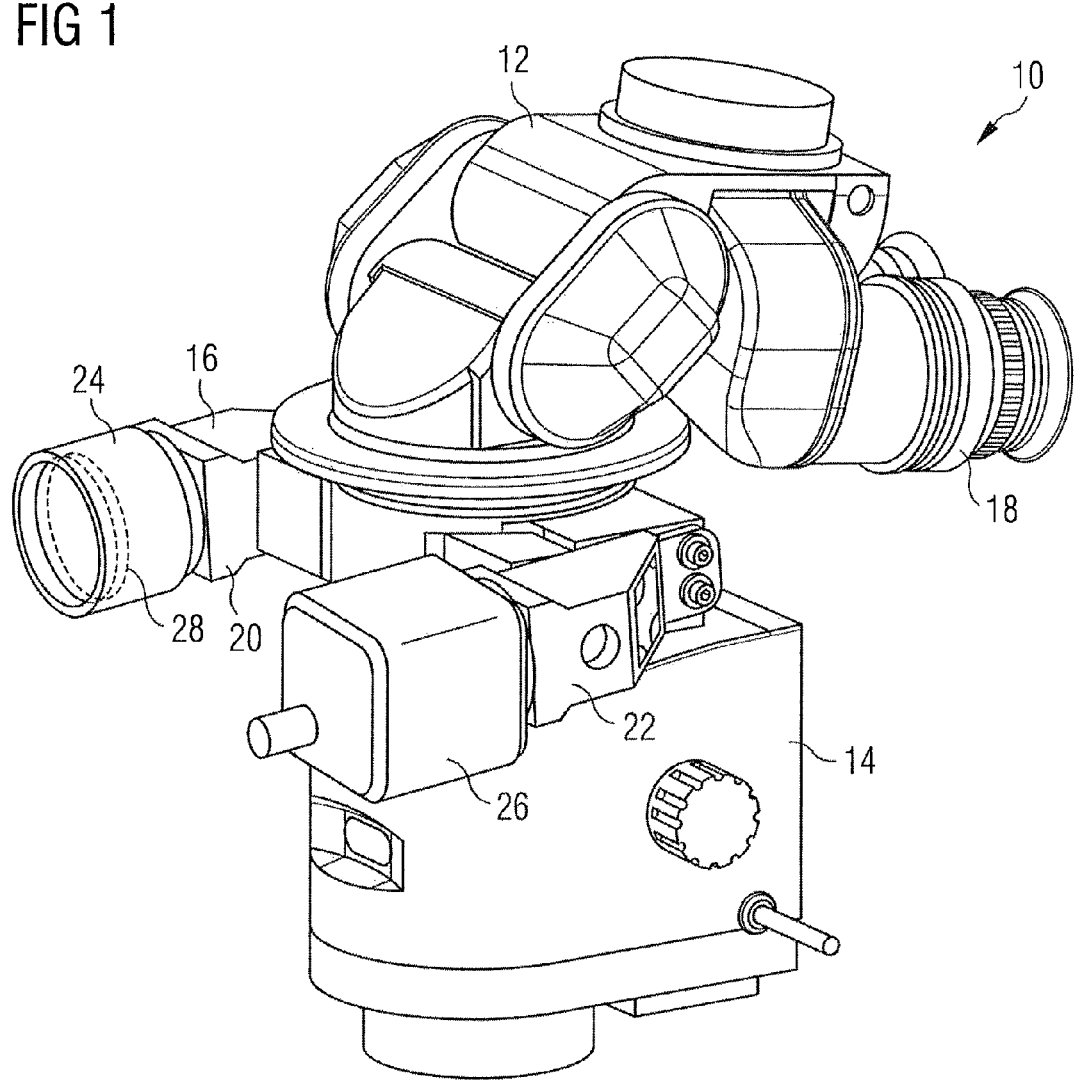
FIG. 1 shows an external perspective view of a surgical microscope according to an exemplary embodiment of the present invention, and FIG. 2 schematically shows the path of different image beams in the surgical microscope of FIG. 1.

The embodiment of the surgical microscope of the present invention shown in FIG. 1, which is denoted overall by 10, can be constructed in a modular fashion and comprises an eyepiece module 12, an objective lens module 14 and an overlay and image acquisition module 16. The latter module 18 is equipped with suitable mechanical interfaces for releasable coupling to the eyepiece module 12 and the objective lens module 14. The eyepiece module 12 has two eyepiece lenses 18 in a manner known per se, only one of which can be seen in the two figures.

The overlay and image acquisition module 16 has two module branches 20, 22, at the ends of which an overlay unit 24 and a camera 26 are respectively fitted. The overlay unit 24 contains an integrated circuit (chip) 28, indicated by dashes, having a combined image display and camera function. In order to fulfil the image display function, the chip 28 can have a multiplicity of image display elements (not represented in detail) produced in OLED-on-CMOS technology, while in order to fulfil the camera function it can be configured with a multiplicity of CMOS-compatible photodetectors (likewise not represented in detail).

The camera 26 may, for example, be a CCD camera.

Figure 2:
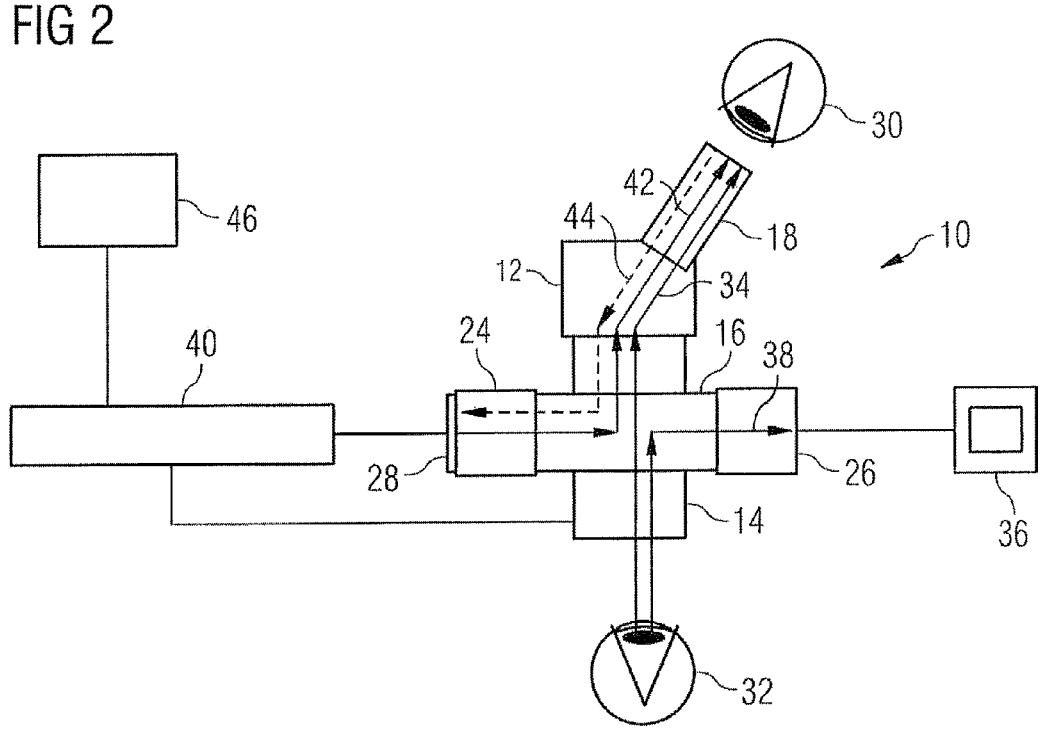

Reference will now also be made to FIG. 2. There, 30 indicates an eye of an observer (operator) while 32 denotes a patient's eye to be treated. The observer views the patient's eye 32 through the surgical microscope 10. An arrow 34 shows the observation beam path of the image of the patient's eye 32.

The camera 26 is used to record an image of the patient's eye 32 and, for example, display it on a monitor 36. A corresponding beam path of the image of the patient's eye 32, recorded by the camera 26, is shown by an arrow 38.

The overlay unit 24 with its combined display/camera chip 28 is used to overlay an image in the form of a control menu having one or more menu options, which the observer can visually select and activate by corresponding eye movements, into the observation field seen by the observer. The image to be overlaid is generated by an electronic control arrangement 40 and delivered to the overlay unit 24 in a suitable signal form. The image to be overlaid is displayed with the aid of the chip 28; the beam path of the image to be overlaid, extending as far as the observer's eye 30, is shown by an arrow 42.

At the same time, the chip 28 records an image of the observer's eye 30 as indicated by a dashed arrow 44. This recorded image is delivered by the overlay unit 24 to the control arrangement 40 and is analysed there with regard to the observer's viewing direction 30 in relation to the overlaid image. In other words, for example, movements of the pupil of the observer's eye 30 are used in order to determine the part of the overlaid image at which the observer is currently looking. If a menu field of the control menu lies in the viewed part of the overlaid image, then a control function assigned to this menu field is executed. The components which can be controlled by visual actuation of the available control functions of the overlaid control menu may differ. In one embodiment, one or more functions of the surgical microscope 10 may be controllable by such visual actuations, for instance a focal function for focusing onto the patient's eye 32. In another embodiment, at least some of the executable control functions may be assigned to medical equipment components separate from the surgical microscope 10. For example, a laser system with which the patient's eye 32 is intended to be treated or a patient table on which the patient lies. Such a separate component is schematically indicated by 46 in FIG. 2.

The visual controllability of the surgical microscope 10 and/or other components, which the doctor uses in an eye operation, overcomes the problem of touching unsterile buttons or knobs and also makes an additional operating staff member superfluous. The workflow is improved because the operator no longer has to take his eyes from the microscope 10 in order to be able to make desired adjustments to the microscope 10 or to other components.

Although embodiments of the proposed apparatus, system and method of the present invention have been illustrated in the accompanying drawings and described in the description, it will be understood that the invention is not limited to the embodiments disclosed herein. In particular, the proposed technique is capable of numerous rearrangements, modifications and substitutions without departing from the scope of the invention as set forth and defined by the following claims.

The invention claimed is:

1. A surgical microscope comprising:
a common module comprising an integrated circuit, the integrated circuit comprising:
an image display module configured to display an image to be overlaid into an observation beam path that goes from an eye of a patient to an eyepiece of the microscope; and
an image sensor configured to record an image of an eye of an observer looking through the eyepiece of the microscope; and
a control arrangement configured to:
receive the recorded image of the eye of the observer; and
analyze the recorded image in relation to the image that was overlaid into the observation beam path to determine a part of the overlaid image that the observer was viewing.

2. The surgical microscope according to claim 1, wherein the common module is produced in CMOS technology and includes image display elements formed by organic light-emitting diodes.

3. The surgical microscope according to claim 2, wherein the image sensor is formed by CMOS-compatible photodetectors.

4. The surgical microscope according to claim 1, wherein the microscope is connected to an electronic control arrangement which is adapted to analyse the image recorded by the image sensor with regard to the observer's viewing direction and to control one or more controllable components as a function of the detected viewing direction of the observer.

5. The surgical microscope according to claim 1, the image to be overlaid and the image of the eye of the observer guided along a common beam path.

6. The surgical microscope according to claim 1:
the image display module comprising a plurality of display elements; and
the image sensor comprising a plurality of photodetectors.

7. The surgical microscope according to claim 1:
the image display module comprising a plurality of display elements; and
the image sensor comprising a plurality of photodetectors, the display elements and the photodetectors arranged as a plurality of interleaved matrices.

8. The surgical microscope according to claim 1, the integrated circuit comprising:
one or more first regions that include a plurality of display elements of the image display; and
one or more second regions that include a plurality of photodetectors of the image sensor.

9. The surgical microscope according to claim 1:
the image display module comprising a plurality of display elements produced using organic light-emitting diode-on-complementary metal-oxide-semiconductor (OLED-on-CMOS) technology; and
the image sensor comprising a plurality of CMOS-compatible photodetectors.

10. The surgical microscope according to claim 1, the control arrangement configured to:
determine that a menu field lies in the part of the overlaid image that the observer was viewing; and
execute a control function assigned to the menu field.

11. A method comprising:
displaying, by an image display module of an integrated circuit, an image to be overlaid into an observation beam path that goes from an eye of a patient to an eyepiece of a surgical microscope; and
recording, by an image sensor of the integrated circuit, an image of an eye of an observer looking through the eyepiece of the microscope;
receiving, by a control arrangement, the recorded image of the eye of the observer; and
analyzing, by the control arrangement, the recorded image in relation to the image that was overlaid into the observation beam path to determine a part of the overlaid image that the observer was viewing.

12. The method according to claim 11, the image to be overlaid and the image of the eye of the observer guided along a common beam path.

13. The method according to claim 11:
the image display module comprising a plurality of display elements; and
the image sensor comprising a plurality of photodetectors.

14. The method according to claim 11:
the image display module comprising a plurality of display elements; and
the image sensor comprising a plurality of photodetectors, the display elements and the photodetectors arranged as a plurality of interleaved matrices.

15. The method according to claim 11, the integrated circuit comprising:
one or more first regions that include a plurality of display elements of the image display; and
one or more second regions that include a plurality of photodetectors of the image sensor.

16. The method according to claim 11:
the image display module comprising a plurality of display elements produced using organic light-emitting diode-on-complementary metal-oxide-semiconductor (OLED-on-CMOS) technology; and
the image sensor comprising a plurality of CMOS-compatible photodetectors.

17. The method according to claim 11, further comprising:
determining, by the control arrangement, that a menu field lies in the part of the overlaid image that the observer was viewing; and
executing a control function assigned to the menu field.

\* \* \* \* \*